United States Patent [19]

Fooladi

[11] 3,950,394

[45] Apr. 13, 1976

[54] M-PHENYLENE-DICARBAMATE

[76] Inventor: Mike Mehdi Fooladi, Apt. 4-B, Oakmont Manor Apts., Vicksburg, Miss. 39180

[22] Filed: Nov. 14, 1974

[21] Appl. No.: 523,686

[52] U.S. Cl. .............................. 260/471 C; 71/111
[51] Int. Cl.² ........................................ C07C 125/06
[58] Field of Search ............................... 260/471 C

[56] References Cited
UNITED STATES PATENTS 3,671,571   6/1972   Koenig et al. .................... 260/471 C

*Primary Examiner*—Lorraine A. Weinberger
*Assistant Examiner*—L. A. Thaxton

[57] ABSTRACT m-Phenylene-N,Ń-methyl-(m-chlorophenyl)-Dicarbamate is synthesized by reaction of resorcinol with methylisocyanate and m-chlorophenylisocyanate. Product is useful for pre-emergence herbicide in agricultural formulation.

1 Claim, No Drawings

M-PHENYLENE-DICARBAMATE

DESCRIPTION OF THE INVENTION

A new chemical compound, namely, m-Phenylene-N,N-methyl-(m-chlorophenyl)-Dicarbamate is found. The product is a compound having the following structural formula:

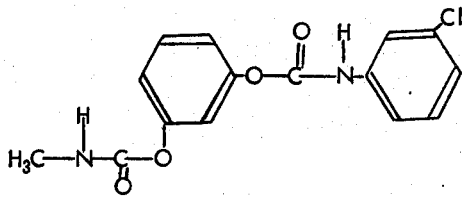

The described compound is prepared by reacting one part of resorcinol with one part of methylisocyanate and one part of m-chlorophenylisocyanate in an inert solvent.

The following example is illustrative of the preparation of the invention compound:

EXAMPLE I

Preparation of m-Phenylene-N,N-methyl-(m-chlorophenyl)-Dicarbamate: A mixture of resorcinol (11.0 g; 0.1 mole), methylisocyanate (6.0 g; 0.1 mole), m-chlorophenylisocyanate (16.0 g; 0.1 mole) and 100 ml benzene was stirred and refluxed for 24 hours. The mixture was cooled then poured into 300 ml of cold water while stirring. The resulting solid material was filtered and dried to give 26 grams of m-Phenylene-N,N-methyl-(m-chlorophenyl)-Dicarbamate, M.P. 161°C–164°C.

Analysis for $C_{15}H_{13}N_2O_4Cl$
| Theory: | | Found: | |
|---|---|---|---|
| C, | 56.16% | C, | 56.50% |
| H, | 4.06% | H, | 3.90% |
| N, | 8.74% | N, | 8.54% |
| Cl, | 11.08% | Cl, | 10.95% |

Concentration of toxicant: The test compounds are formulated by a standard procedure of solution in acetone, addition of an emulsifier, and dilution with water. The results of screening tests are tabulated in Table I.

TABLE 1

| Invented Compound | Rate Lbs./A | Herbicidal Screening Tests | | | | | | | | | | | | | | |
|---|---|---|---|---|---|---|---|---|---|---|---|---|---|---|---|---|
| | | Mustard | | Pigweed | | Crabgrass | | Foxtail | | Corn | | Wheat | | Cotton | | Beans |
| | | Pre | Post | Pre | Post | Pre | Post | Pre | Post | Pre | Post | Pre | Post | Pre | Post | Pre | Post |
| " | 10 | 2RG | — | 2RG | — | 1RG | — | 0 | — | 0 | — | 2RG | — | 1RG | — | 0 | — |
| " | 5 | 2RG | — | 2RG | — | 0 | — | 0 | — | 0 | — | 1RG | — | 0 | — | 0 | — |

The letter ratings in Table I are:
O = None
2RG = Moderate reduced germination
1RG = Slight reduced germination

I claim:
1. Dicarbamate having the general formula

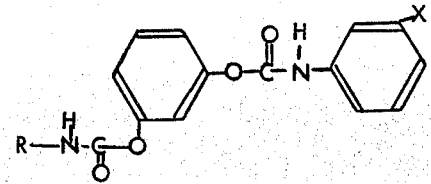

wherein R is a methyl group and X designates a chlorine.

* * * * *